(12) United States Patent
Csutak

(10) Patent No.: US 8,358,414 B2
(45) Date of Patent: Jan. 22, 2013

(54) DOWNHOLE SENSORS USING MANUFACTURED ANISOTROPIC PERMITTIVITY

(75) Inventor: Sebastian Csutak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 262 days.

(21) Appl. No.: 12/758,545

(22) Filed: Apr. 12, 2010

(65) Prior Publication Data
US 2010/0220324 A1 Sep. 2, 2010

Related U.S. Application Data

(63) Continuation-in-part of application No. 11/776,165, filed on Jul. 11, 2007, now Pat. No. 7,751,044.

(51) Int. Cl.
G01J 4/00 (2006.01)
(52) U.S. Cl. .......................................... 356/365; 356/33
(58) Field of Classification Search ................... 356/365, 356/432
See application file for complete search history.

(56) References Cited

U.S. PATENT DOCUMENTS

| | | | |
|---|---|---|---|
| 4,048,859 A * | 9/1977 | Babcock ..................... 73/514.27 |
| 4,171,908 A * | 10/1979 | Robert et al. .................... 356/33 |
| 4,215,576 A | 8/1980 | Quick et al. |
| 4,215,578 A * | 8/1980 | Lautzenhiser .............. 73/382 G |
| 4,233,847 A | 11/1980 | Walker |
| 5,134,882 A | 8/1992 | Taylor |
| 5,177,555 A | 1/1993 | Stratton et al. |
| 5,202,745 A | 4/1993 | Sorin et al. |
| 5,410,917 A | 5/1995 | Giversen et al. |
| 5,912,457 A * | 6/1999 | McQuaid ................. 250/227.17 |
| 6,437,916 B1 | 8/2002 | McLeod et al. |
| 6,567,174 B1 | 5/2003 | Barker et al. |
| 6,597,821 B1 | 7/2003 | Bohnert et al. |
| 6,779,402 B2 | 8/2004 | Rud et al. |
| 6,789,424 B2 | 9/2004 | Knudsen et al. |
| 6,813,064 B2 * | 11/2004 | John et al. ...................... 359/321 |
| 6,816,534 B2 | 11/2004 | Flint et al. |
| 2002/0097371 A1 | 7/2002 | Yoshino |
| 2004/0129867 A1* | 7/2004 | Mackey ......................... 250/225 |
| 2006/0152209 A1* | 7/2006 | Sasaki et al. .................... 324/96 |
| 2007/0126594 A1* | 6/2007 | Atkinson et al. ........... 340/853.1 |
| 2009/0015834 A1 | 1/2009 | Csutak |
| 2009/0114014 A1 | 5/2009 | Csutak |

OTHER PUBLICATIONS

Limeres J. Calvo ML, Lakshminarayanan V. et al., Stress sensor based on light scattering by an array of birefringent optical waveguides 19th Congress of the International Commission for Optics, Aug. 25-30, 2002.
International Search Report for International Application No. PCT/US2008/069315, Mailed Sep. 3, 2008.
Written Opinion of the International Searching Authority for International Application No. PCT/US2008/069315, Mailed Sep. 3, 2008.

* cited by examiner

*Primary Examiner* — Gregory J Toatley
*Assistant Examiner* — Dominic J Bologna
(74) *Attorney, Agent, or Firm* — Mossman Kumar & Tyler PC

(57) ABSTRACT

A apparatus for use in a borehole in an earth formation. The apparatus may include: an electromagnetic source; an anisotropic permittivity material, either natural or manufactured, receiving electromagnetic radiation from the electromagnetic source; and a detector for estimating the electromagnetic radiation transmitted through the anisotropic permittivity material as an indication of a parameter of interest. Also, a method of estimating a parameter of interest using the aforementioned apparatus.

20 Claims, 8 Drawing Sheets

DOWNHOLE SENSORS USING MANUFACTURED ANISOTROPIC PERMITTIVITY

CROSS REFERENCE TO RELATED APPLICATION

This application is a continuation-in-part of U.S. patent application Ser. No. 11/776,165, for "Optical Sensor for Downhole Measurements Using Birefringent Materials", published as U.S. 2009-0015834, filed on Jul. 11, 2007, and claims the benefit of priority from the aforementioned application.

FIELD OF THE DISCLOSURE

This disclosure generally relates to exploration for hydrocarbons involving investigations of a borehole penetrating an earth formation, and estimating parameters of interest from within the borehole.

BACKGROUND OF THE DISCLOSURE

In exploration for hydrocarbons, it is important to make accurate measurements of geologic formations. The geologic formations below the surface of the earth may contain reservoirs of oil and gas. The geologic formations may include formation bedding planes and various structures. In a quest for oil and gas, it is important to know about the location and composition of the formation bedding planes and the various structures. In particular, it is important to know about the geologic formations with a high degree of accuracy so that reservoir production is optimized. Measuring properties of the geologic formations provides information that can be useful for locating the reservoirs of oil and gas. Typically, the oil and gas are retrieved by drilling boreholes into the subsurface of the earth. The boreholes also provide access for taking measurements of the geologic formations.

Well logging is a technique used to take measurements of the geologic formations from the borehole. In one embodiment, a "logging instrument" is lowered on the end of a wireline into the borehole. The logging instrument sends data via the wireline to the surface for recording. Output from the logging instrument comes in various forms and may be referred to as a "log." Many types of measurements are made to obtain information about the geologic formations. Some examples of the measurements include gamma ray logs, nuclear magnetic resonance logs, resistivity logs, pressure logs, and sonic or acoustic logs.

With today's sophisticated drilling and logging techniques, it is important to have an accurate orientation of the logging tool in the borehole. For example, the boreholes may be deviated from a vertical plane and even horizontal. As one might imagine, in a horizontal borehole, it is important to know whether one is taking measurements of the formations above or below the borehole. Even in vertical boreholes, it is important to know the orientation of certain measurements so that the orientation of the formations with respect to the borehole may be discerned.

Typically, data from several logging tools are analyzed side-by-side to form a composite picture of the formations. Even small errors in the orientation of the logging tool can corrupt logging data. An assumption that the logging instrument is moving smoothly through the borehole is not always valid due to rugose and sticky borehole conditions. Additionally, tool centralizers and decentralizers may keep the logging tool from moving smoothly and contribute to disorientation.

Sensors are needed to determine the orientation of the logging tool. The sensors may also be used to measure acceleration due to external perturbations acting upon the logging tool. Data from measuring the acceleration can be used to determine the orientation of the logging tool.

It is also important to measure pressure at various depths within the borehole. If the pressure is not kept under control, then an uncontrolled release of oil and gas to the surface (known as a "blowout") can result. The blowout can cause personal injuries, drilling rig damage, environmental damage, and damage to underground reservoirs. Pressure sensors are needed to monitor the pressure within the borehole.

Conditions hostile to sensors within the logging instrument exist in the boreholes. For example, high temperatures and pressure may cause the sensors to fail. Failure of sensors such as the accelerometers and pressure sensors in the borehole can lead to wasting a significant amount of resources.

What are needed are an apparatus and a method for making accurate measurements of acceleration and pressure in the borehole.

SUMMARY OF THE DISCLOSURE

The shortcomings of the prior art are overcome and additional advantages are provided through an apparatus for estimating a parameter of interest, the apparatus including a light source; a birefringent material receiving light from the source; and a photodetector for measuring light transmitted through the birefringent material to measure the at least one of orientation, acceleration and pressure.

Also disclosed is a method for measuring at least one of orientation, acceleration and pressure, the method including measuring light transmitted through a birefringent material; and correlating measurement of the light to at least one of orientation, acceleration, and pressure.

Also disclosed is a computer program product stored on machine-readable media, the product includes instructions for measuring at least one of orientation, acceleration and pressure, the instructions include instructions for measuring light transmitted through a birefringent material; and correlating measurement of the light to at least one of orientation, acceleration, and pressure.

Further disclosed is a method for producing a logging instrument adapted for measuring at least one of orientation, acceleration and pressure in a borehole, the method including selecting at least one sensor comprising a light source, a birefringent material, and a photodetector; and placing the sensor into the instrument.

Another embodiment according to the present disclosure includes an apparatus for use in a borehole, comprising: a manufactured anisotropic permittivity material; and a detector configured to receive electromagnetic radiation transmitted through the manufactured anisotropic permittivity material and generate a signal in response thereto.

Another embodiment according to the present disclosure includes a method for estimating a parameter of interest, the method comprising: operating a sensor positioned in a borehole, comprising: a manufactured anisotropic permittivity material; and a detector configured to receive electromagnetic radiation transmitted through the manufactured anisotropic permittivity material and generate a signal in response thereto.

Another embodiment according to the present disclosure includes a computer product, comprising: a processor; and a set of instructions that, when executed, cause the processor to perform a method, the method comprising: estimating the parameter of interest using an apparatus comprising: a manufactured anisotropic permittivity material; and a detector configured to receive electromagnetic radiation transmitted through the manufactured anisotropic permittivity material and generate a signal in response thereto.

Another embodiment according to the present disclosure includes a method for manufacturing an apparatus for estimating a parameter of interest, comprising: forming the apparatus by operatively coupling a detector and a medium, wherein the permittivity of the medium has been artificially altered in at least one direction.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION OF THE DISCLOSURE

Figure 1:
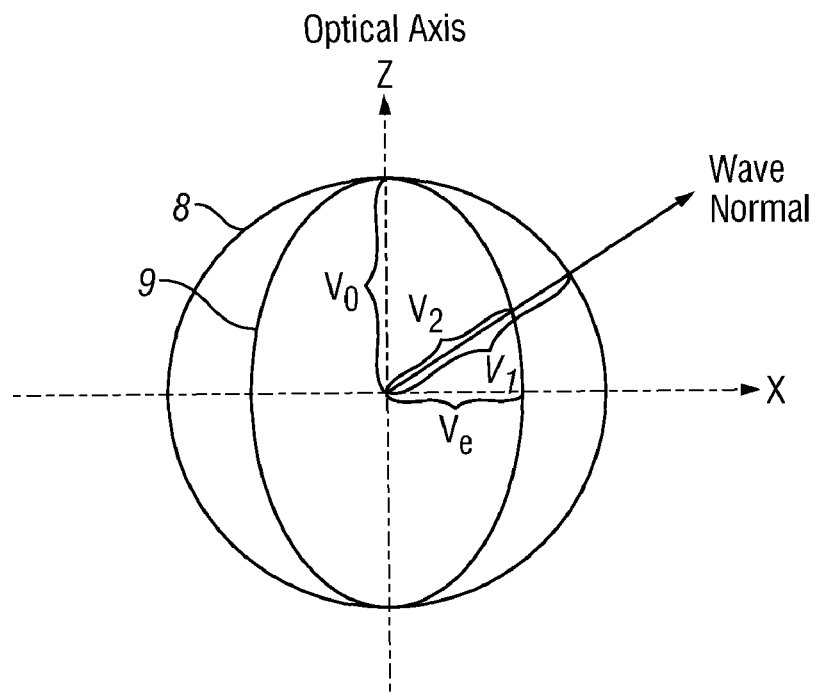
FIG. 1 illustrates an exemplary embodiment of two geometric surfaces representing velocities of a light ray with a wave normal direction in a uniaxial crystal that is optically positive.

The teachings provide an apparatus and method for estimating a parameter of interest. The parameter of interest may be associated with an earth formation. The parameter of interest may include, but is not limited to, one of: mechanical force, temperature, magnetism, electric potential, electric current, pressure, acceleration, gravity, electromagnetic radiation, nuclear radiation, and vibration. The apparatus may include at least one of: a manufactured anisotropic permittivity (MAP) material and a material that demonstrates natural anisotropic permittivity NAP. The MAP/NAP material may be sensitive to at least one of direction of light transmitted through the material and at least one form of stimulus. Herein, transmission through the MAP/NAP material may include at least partial passage through the MAP/NAP material. Stimuli that the MAP/NAP material may be sensitive to include, but are not limited to, mechanical force, temperature, magnetism, electric potential, electric current, pressure, acceleration, gravity, electromagnetic radiation, nuclear radiation, and vibration. Also, the term "light" used herein refers to all forms of electromagnetic radiation, including those outside the visible light spectrum. The MAP/NAP material affects light transmitted/reflected through the MAP/NAP material. The light is affected in relation to at least one of direction of light transmitted and an amount of stimulus exerted upon the MAP/NAP material. The effect on the light transmitted/reflected through the MAP/NAP material can be measured and correlated to at least one of the direction of light transmitted/reflected through the MAP/NAP material and the stimulus exerted on the MAP/NAP material. The teachings herein call for the MAP/NAP materials to exhibit anisotropic permittivity, such as birefringence. Before the apparatus and method are discussed in detail, certain definitions are provided with respect to anisotropic permittivity and birefringence.

Anisotropic permittivity refers to the property of some materials that permittivity is dependent on the direction of light rays entering the material demonstrating anisotropic permittivity. The term "birefringence" relates to an optical material that is anisotropic, such that birefringence may be considered a subset of anisotropic permittivity, since birefringence may be commonly associated with visible light and anisotropic permittivity may occur anywhere along the electromagnetic spectrum. Herein, anisotropic permittivity may be discussed, at times, in terms of birefringence, however, this disclosure envisions the operation of these principles applying to all forms of anisotropic permittivity, including those operating at frequencies lower than optical frequencies such as millimeter waves or radio waves.

Optical properties of a "birefringent" material are dependent upon a direction of light rays entering the birefringent material. An "optical axis" relates to defining the direction that affects the light rays entering the birefringent material. Light entering a birefringent material parallel to an optical axis is not affected by the birefringent material. Light entering the birefringent material at an angle that is not parallel to the optical axis is affected by the birefringent material. In general, an incident light ray entering the birefringent material not parallel to the optical axis is decomposed into two light rays. One light ray may be polarized perpendicular to the optical axis. The light ray polarized perpendicular to the optical axis is referred to as an "ordinary ray." The other light ray is polarized parallel to the optical axis. The light ray polarized parallel to the optical axis is referred to as an "extraordinary ray." The ordinary ray and the extraordinary ray travel at different speeds. The different speeds of the ordinary ray and the extraordinary ray gives rise to a double refraction property exhibited by the birefringent material. Definitions of different types of MAP/NAP materials are presented next.

One type of MAP/NAP material exhibits photoelasticity. The term "photoelasticity" relates to a birefringent material exhibiting birefringence when induced with mechanical stress. The mechanical stress may be at least one of tensile and compressive. Materials exhibiting photoelasticity are referred to as "photoelastic."

Another type of MAP/NAP material exhibits photoresponsivity. The "photoresponisivity" relates to a MAP/NAP material exhibiting anisotropic permittivity when induced with a stimulus. The stimulus may be one or more of, but not limited to, mechanical force, temperature, magnetism, electric potential, electric current, pressure, acceleration, gravity, electromagnetic radiation, nuclear radiation, and vibration. Materials exhibiting photoresponsivity are referred to as "photoresponsive." As used herein, the photoelasticity is a subset of photoresponsivity.

Another type of MAP/NAP material may have one of uniaxial and biaxial properties. A MAP/NAP material with one or more uniaxial or biaxial properties may be crystalline, non-crystalline (including plastics), or a combination thereof (such as air/crystal or glass/crystal). The term "uniaxial" relates to birefringent materials with one optical axis. The term "biaxial" relates to birefringent materials that have two optical axes. Properties of the ordinary ray and the extraordinary ray traveling through a uniaxial crystal or a biaxial crystal may be described by an "ellipsoid of wave normals." The ellipsoid of wave normals is an ellipsoid (or geometric surface) that shows a velocity and a vibration direction for each of the ordinary ray and the extraordinary ray traveling through the birefringent material. An index of refraction can be calculated from the velocity. With the index of refraction, a direction of travel can be determined for each of the ordinary ray and the extraordinary ray. Table 1 illustrates a list of crystal structures and for each crystal structure an associated ellipsoid of wave normals and an optical classification.

TABLE 1

| Crystal System | Ellipsoid of Wave Normals | Optical Classification |
| --- | --- | --- |
| Triclinic | General ellipsoid | Biaxial |
| Monoclinic | General ellipsoid | Biaxial |
| Orthorhombic | General ellipsoid | Biaxial |
| Trigonal | Spheroid | Uniaxial |
| Tetragonal | Spheroid | Uniaxial |
| Hexagonal | Spheroid | Uniaxial |

Equations (1) and (2) can be used to describe a light ray traveling through a birefringent material that is a uniaxial crystal:

$$v_1^2 = v_o^2 \quad (1)$$

$$v_2^2 = v_o^2 \cos^2\theta + v_e^2 \sin^2\theta \quad (2)$$

where $v_1$ is the velocity of a first light ray, $v_2$ is the velocity of a second light ray, the Z-axis is the optical axis, $v_o$ is the velocity of a light ray with vibrations in the X-Y plane, $v_e$ is the velocity of a light ray with vibrations in a plane parallel to the Z-axis, and $\theta$ is the angle of the incident light ray with respect to the optical axis. From equations (1) and (2), the light ray traveling through the uniaxial crystal is separated into two light rays, the ordinary ray and the extraordinary ray. The ordinary ray has velocity $v_1$ that is independent of $\theta$. The extraordinary ray has velocity $v_2$ that is dependent on $v_o$, $v_e$, and $\theta$. The velocity of the ordinary ray and the velocity of the extraordinary ray are equal when $\theta$ equals zero. The uniaxial crystals are further classified with respect to the relationship between $v_o$ and $v_e$.

If $v_o$ is greater than $v_e$, then the ordinary ray travels faster than the extraordinary ray (except when $\theta$ equals zero). When $v_o$ is greater than $v_e$, the uniaxial crystal is referred to as "optically positive." Quartz is one example of the uniaxial crystal that is optically positive. FIG. 1 illustrates an exemplary embodiment of two geometric surfaces representing wave normals of the uniaxial crystal that is optically positive. Referring to FIG. 1, a sphere 8 represents the velocity $v_1$ of the ordinary ray. Also referring to FIG. 1, an ovaloid 9 represents the velocity $v_2$ of the extraordinary ray. Because $v_o$ is greater than $v_e$, the ovaloid 9 is contained within the sphere 8.

Figure 2:
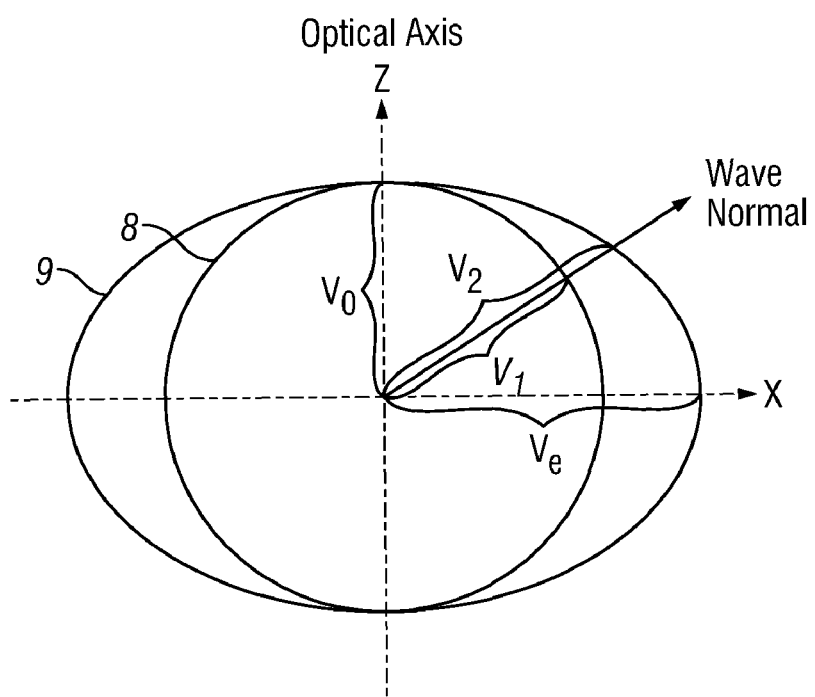
FIG. 2 illustrates an exemplary embodiment of two geometric surfaces representing velocities of the light ray with the wave normal direction in a uniaxial crystal that is optically negative.

If $v_e$ is greater than $v_o$, then the extraordinary ray travels faster than the ordinary ray. When $v_e$ is greater than $v_o$, the uniaxial crystal is referred to as "optically negative." Feldspar is one example of the uniaxial crystal that is optically negative. FIG. 2 illustrates an exemplary embodiment of two geometric surfaces representing wave normals of the uniaxial crystal that is optically negative. Because $v_e$ is greater than $v_o$, the sphere 8 is contained within the ovaloid 9.

Figure 3:
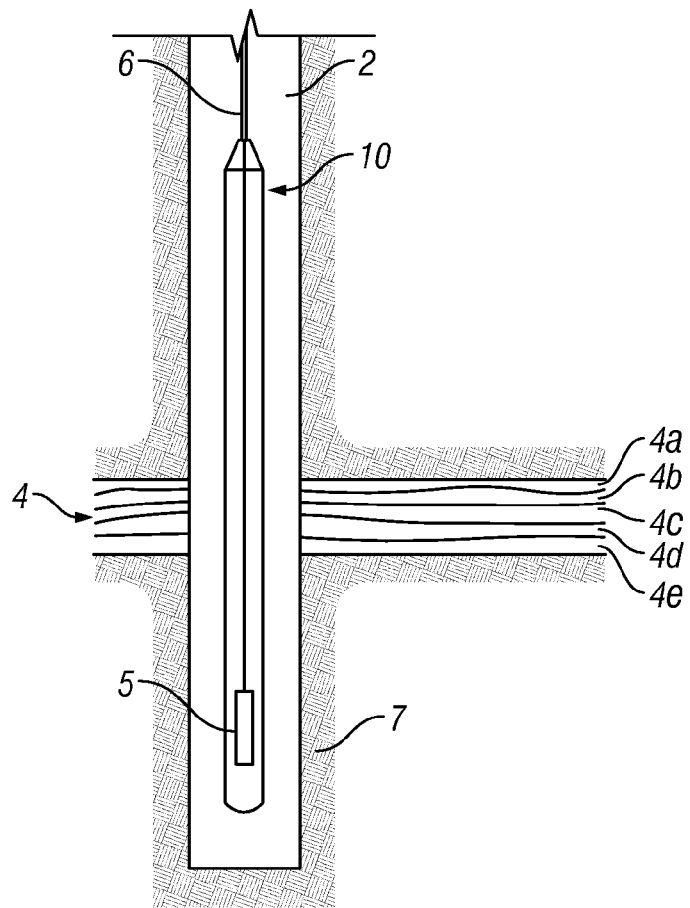
FIG. 3 illustrates an exemplary embodiment of a logging instrument in a borehole penetrating the earth.

Referring to FIG. 3, a well logging instrument 10 is shown disposed in a borehole 2. The borehole 2 is drilled through earth 7 and penetrates formations 4, which include various formation bedding planes 4A-4E. The logging instrument 10 is typically lowered into and withdrawn from the borehole 2 by use of an armored electrical cable 6 or similar conveyance as is known in the art. A sensor 5 is shown disposed within the logging instrument 10. In one embodiment, the sensor 5 may be used for measuring, but is not limited to one of orientation, acceleration and pressure.

For the purposes of this discussion, it is assumed that the borehole 2 is vertical and that the formations 4 are horizontal. The apparatus and method however can be applied equally well in deviated or horizontal wells or with the formation bedding planes 4A-4E at any arbitrary angle. The apparatus and method are equally suited for use in LWD applications and in open-borehole and cased-borehole wireline applications. In LWD applications, the apparatus may be disposed in a drilling collar. This apparatus and method may be used in a borehole for long term monitoring.

Figure 4A:
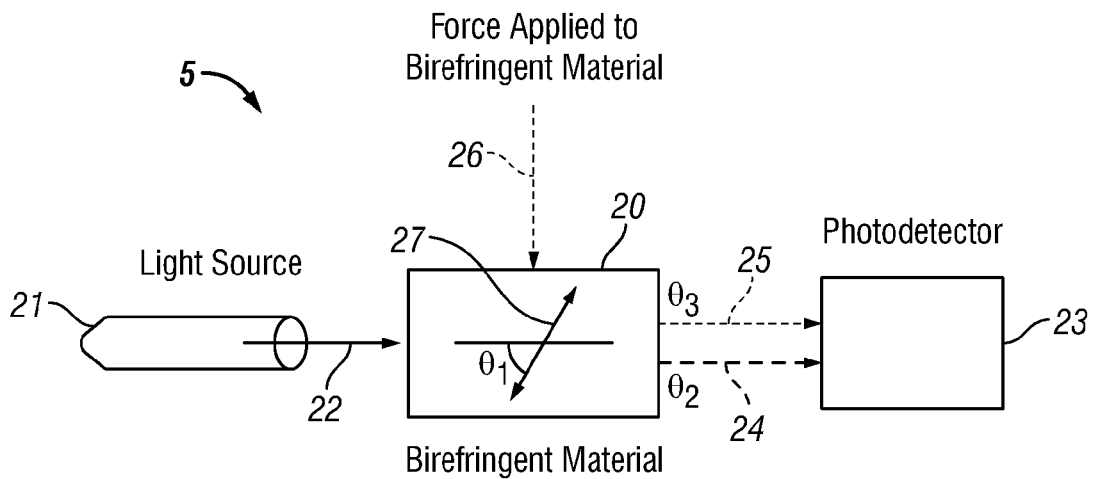
FIGS. 4A, 4B, and 4C, collectively referred to as FIG. 4, illustrate exemplary aspects of a sensor.

FIG. 4 illustrates an exemplary schematic diagram of the sensor 5 for measuring force where the force may be at least one of orientation, acceleration and pressure. Referring to FIG. 4A, the sensor 5 includes a light source 21, a birefringent material 20, and a photodetector 23. In general, when used for measuring force, the birefringent material 20 may be photoelastic. When measuring a stimulus other than, or in addition to, force, such as magnetism or electric current, the birefringent material 20 may be photoresponsive. An exemplary embodiment of the birefringent material 20 that is photoelastic is a clear plastic. The light source 21 provides a beam of light, referred to as incident light ray 22, for transmission through the birefringent material 20. Typically, the light source 21 provides a narrow beam of light such as that produced by a laser, however, other light sources including collimated light sources and even nondirectional or incoherent light sources may be used. Referring to FIG. 2A, the birefringent material 20 decomposes the beam of light into two beams of light, an ordinary ray 24 and an extraordinary ray 25. Characteristics of the ordinary ray 24 and the extraordinary ray 25 are related to a force 26 applied to the birefringent material 20. In this embodiment, the force 26 causes the birefringent material 20 to flex a certain amount. In other embodiments, a stimulus may act upon the MAP/NAP material to simply alter the character of the light beam traversing the MAP/NAP material with or without flexing of the MAP/NAP material. In some embodiments, the MAP/NAP material may be a solid, a liquid, a gas, or a combination. In general, the ordinary ray 24 and the extraordinary ray 25 have polarizations different from each other. The photodetector 23 measures at least one of intensity, polarization, and exit angle for the ordinary ray 24 and the extraordinary ray 25. For measuring polarization, the photodetector 23 may include at least one of a polarimeter and a polarizer. The polarimeter may be based on at least one of an interferometer and an arrangement of polarizing filters and/or wave guides. In one embodiment, a Nichol prism is used to measure the characteristics of the ordinary ray 24 and the extraordinary ray 25. The Nichol prism can be set to measure the characteristics of the ordinary ray 24. The Nichol prism can then be rotated ninety degrees to measure the characteristics of the extraordinary ray 25. Measurements by the photodetector 23 are typically correlated to the force 26. Therefore, the force 26 acting upon the birefringent material 20 can be determined by measuring the characteristics of the ordinary ray 24 and the extraordinary ray 25.

FIG. 4A also illustrates an optical axis 27 of the birefringent material 20. Some optical characteristics of the ordinary ray 24 and the extraordinary ray 25 are determined by an angle $\theta_1$ the incident ray 22 makes with the optical axis 27. The optical characteristics include intensity and exit angle for the ordinary ray 24 and the extraordinary ray 25.

Figure 4B:
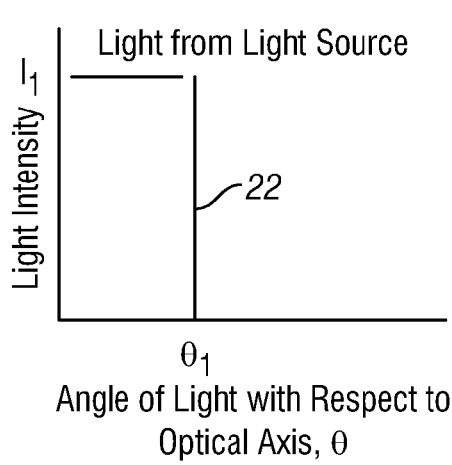

FIG. 4B illustrates an exemplary graph of light intensity versus angle of light with respect to the optical axis 27 for the incident light ray 22. The incident light ray 22 of intensity $I_1$ is incident to the optical axis 27 at the angle $\theta_1$.

Figure 4C:
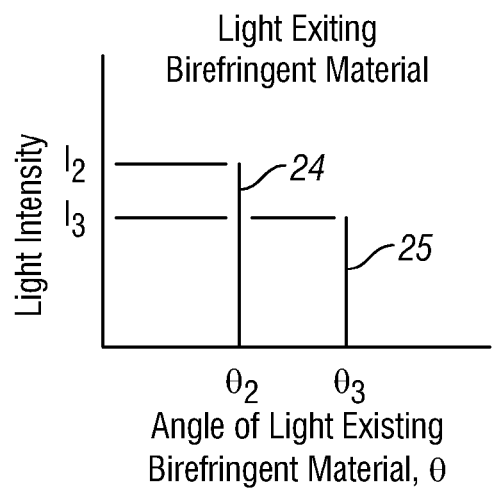

FIG. 4C illustrates an exemplary graph of light intensity versus exit angle for the ordinary ray 24 and the extraordinary ray 25. The exit angle may be measured with respect to the optical axis 27 or a surface of the birefringent material 20. The ordinary ray 24 exits the birefringent material 20 with intensity $I_2$ and exit angle $\theta_2$. The extraordinary ray 25 exits the birefringent material 20 with intensity $I_3$ and exit angle $\theta_3$. Typically, when the incident light 22 is incident to the optical axis 27 at an angle other than zero degrees or ninety degrees, the exit angles $\theta_2$ and $\theta_3$ are not the same. In general, a change in the force 26 acting upon the birefringent material 20 in the direction of the optical axis 27 will cause $I_2$, $\theta_2$, $I_3$, and $\theta_3$ to shift. The shift in $I_2$, $\theta_2$, $I_3$, and $\theta_3$ can be correlated to the change in the force 26. In general, forces acting upon the sensor 5 are transmitted directly to the birefringent material 20. Therefore, with knowledge of the mass of the sensor 5, the change in the force 26 can be correlated to an acceleration of the sensor 5. For embodiments measuring pressure, the change in the force 26 can be correlated to a change in pressure.

Figure 5:
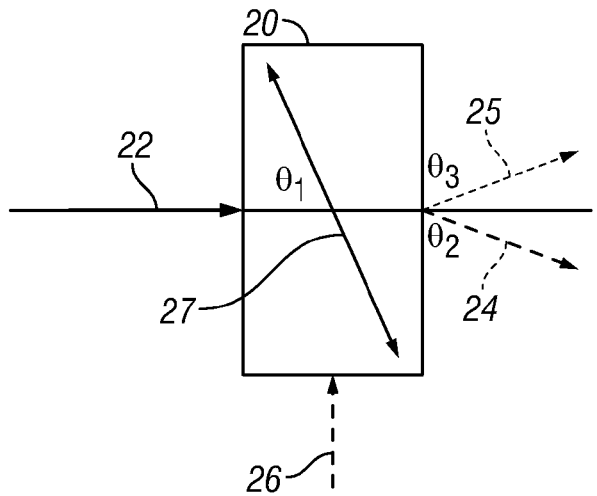
FIG. 5 illustrates an exemplary embodiment of a birefringent material that is photoelastic.

FIG. 5 illustrates an exemplary embodiment of the birefringent material 20 that is uniaxial. Referring to FIG. 3, the incident light ray 22 is not normal to the optical axis 27. The incident light ray 22 is decomposed into two divergent light rays, the ordinary ray 24 and the extraordinary ray 25. The intensity and the exit angle of each of the two divergent light rays is related to an amount of the force 26 that is applied to the birefringent material 20.

Figure 6:
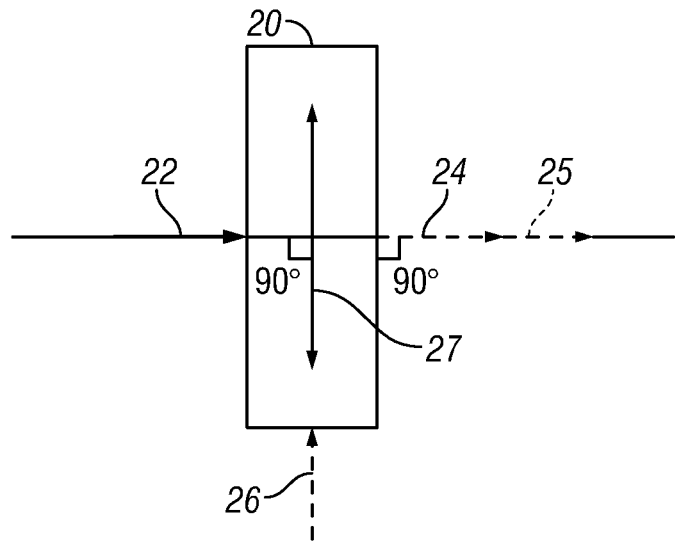
FIG. 6 illustrates an exemplary embodiment of the birefringent material with incident light normal to an optical axis.

FIG. 6 illustrates another exemplary embodiment of the birefringent material 20 that is uniaxial. Referring to FIG. 4, the incident light ray 22 is normal to the optical axis 27. The incident light ray 22 is decomposed into two light rays, the ordinary ray 24 and the extraordinary ray 25. The ordinary ray 24 and the extraordinary ray 25 each have the same exit angle and are superimposed upon each other. The ordinary ray 24 and the extraordinary ray 25 have different polarizations. Therefore, the intensity of the ordinary ray 24 and the extraordinary ray 25 can be measured using at least one Nichol prism. The amount of birefringence in a given direction is related to the amount of the force 26 applied to the birefringent material 20.

As discussed above, the sensor 5 may be used to measure pressure. Embodiments of the birefringent material 20 that are spherical in shape can be used to measure pressure. The force 26 may be derived from the pressure acting on the logging instrument 10. The spherical shape provides for evenly distributing the force 26 about the surface of the birefringent material 20. The pressure may be measured by at least one of intensity and exit angle of the ordinary ray 24 and the extraordinary ray 25.

Figure 7:
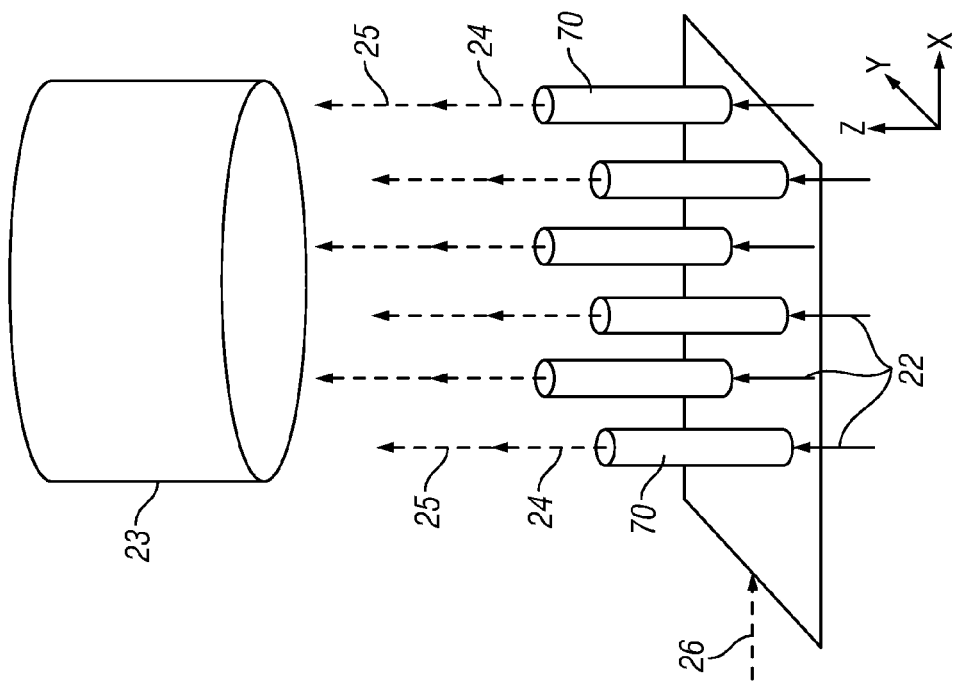
FIG. 7 illustrates an exemplary embodiment of an array of optical fibers exhibiting photoelasticity.

The sensor 5 may be built to include at least one optical fiber that exhibits photoelasticity. FIG. 7 illustrates an exemplary embodiment of the sensor 5 that includes an array of optical fibers 70 that exhibit photoelasticity. Specifically, the optical fibers 70 act as a uniaxial crystal when stressed mechanically. The array of optical fibers 70 produces stronger signals that are more easily detectable than the signals produced by a single optical fiber 70. The array of the optical fibers 70 is arranged to transmit light in the Z-direction. The diameter of the optical fiber 70 may be about 9 μm (typical core size of a single mode fiber) or other size commonly used by one of skill in the art. The diameter of optical fiber 70 may be sized to be about 5 to about 10 wavelengths of the incident light rays 22. Separation between the optical fibers 70 may be about 50 μm. The force 26 induces mechanical stress in the optical fibers 70 in the X-Y plane. The mechanical stress may cause deflection of the optical fibers 70. At least one of the mechanical stress and the deflection causes the optical fibers 70 to decompose the incident light rays 22 into the ordinary rays 24 and the extraordinary rays 25. Typically, the ordinary rays 24 and the extraordinary rays 25 are scattered forward towards the photodetector 23. An intensity of the ordinary rays 24 and the extraordinary rays 25 is typically measured with the photodetector 23. The intensity of the ordinary rays 24 and the extraordinary rays 25 and the amount of birefringence can be correlated to the force 26. Further, a force acting upon the sensor 5 can be correlated to the force 26 in terms of a relationship. With knowledge of the relationship, the force 26, and the mass of the sensor 5, the acceleration experienced by the sensor 5 can be determined.

Referring to FIG. 7, the photodetector 23 may be at least one of optically and mechanically coupled to the optical fibers 70. With mechanical coupling, the optical fibers 70 may be allowed to deflect in generally the X-Y plane and insure that the ordinary rays 24 and the extraordinary rays 25 enter the photodetector 23.

Figure 8:
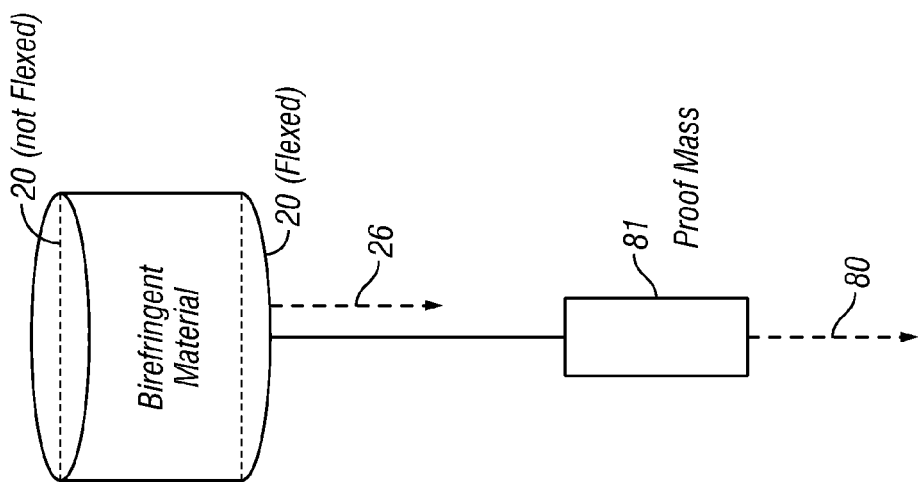
FIG. 8 illustrates an exemplary embodiment of a proof mass connected to the birefringent material.

The sensor 5 can also be used to measure gravitational acceleration. Typically, in embodiments of the sensor 5 that measure gravitational acceleration, a proof mass is connected to the birefringent material 20. FIG. 8 illustrates an exemplary embodiment of aspects of the sensor 5 used for measuring gravitational acceleration. Referring to FIG. 8, a gravitational force 80 related to the gravitational acceleration acts upon a proof mass 81. The proof mass 81 in turn applies the force 26 upon the birefringent material 20. A connection between the proof mass 81 and the birefringent material 20 may be at least one of a flexible connection such as a cable and a rigid connection such as a lever. As discussed above, the force 26 can be determined by measuring the characteristics of the ordinary ray 24 and the extraordinary ray 25 exiting the birefringent material 20. With knowledge of a relationship between the gravitational force 80 and the force 26, the gravitational acceleration acting upon the sensor 5 can be determined.

The sensor 5 may be used to measure relative gravitational acceleration and absolute gravitational acceleration. Measurement of relative gravitational acceleration involves comparing the gravitational force 80 to a reference. The relative gravitational acceleration relates to a change in the gravitational force 80. Measurement of absolute gravitational acceleration involves calibrating the sensor 5 to an absolute standard of the gravitational acceleration to provide a calibration point. The calibration involves correlating the absolute gravitational acceleration to the force 26 acting upon the proof mass 81. The absolute gravitational acceleration at a location can then be measured by determining a difference in the gravitational force 80 from the calibration point.

Figure 9A:
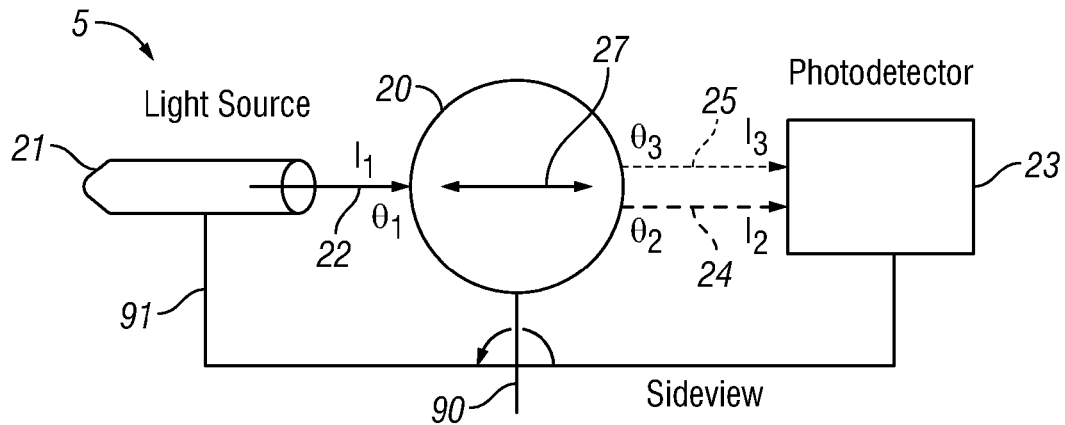
FIGS. 9A, 9B, and 9C, collectively referred to as FIG. 9, illustrate exemplary aspects of the sensor used for measuring orientation.

As discussed above, the sensor 5 can also be used for measuring orientation. Typically, the orientation of one frame of reference is measured with respect to another frame of reference. One example of orientation is an amount of rotation of one body with respect to another body. FIG. 9 illustrates an exemplary embodiment of the sensor 5 used for measuring orientation. FIG. 9A illustrates a side view of the sensor 5. Referring to FIG. 9A, the sensor 5 includes the light source 21 rigidly attached to the photodetector 23 via connection 91. The embodiment of FIG. 9 allows rotation of the light source 21 and the photodetector 23 with respect to the birefringent material 20 about a rotation axis 90. In the exemplary embodiment of FIG. 9, the birefringent material 20 is a uniaxial crystal and spherically shaped. The crystal is spherically shaped so that distances between the light source 21 and the birefringent material 20 and between the photodetector 23 and the birefringent material 20 are kept constant. Exemplary embodiments of the birefringent material 20 include lithium niobate, potassium dihydrogen phosphate, gallium arsenide, indium phosphide, gallium nitride, and silicon carbide.

Figure 9B:
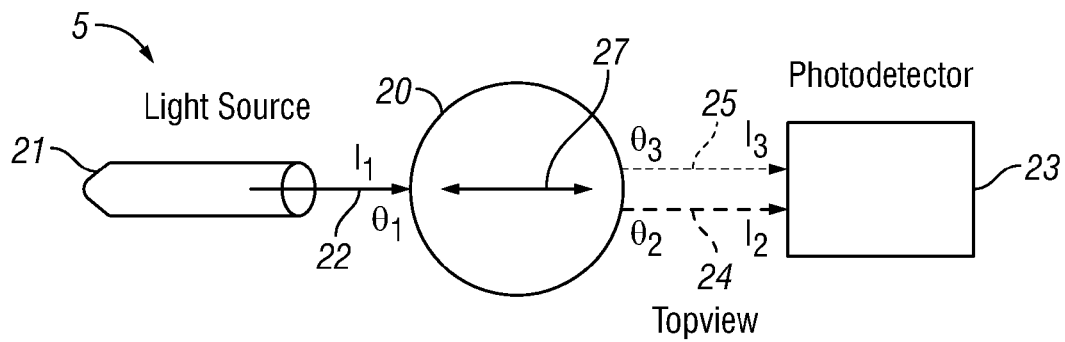
Figure 9C:
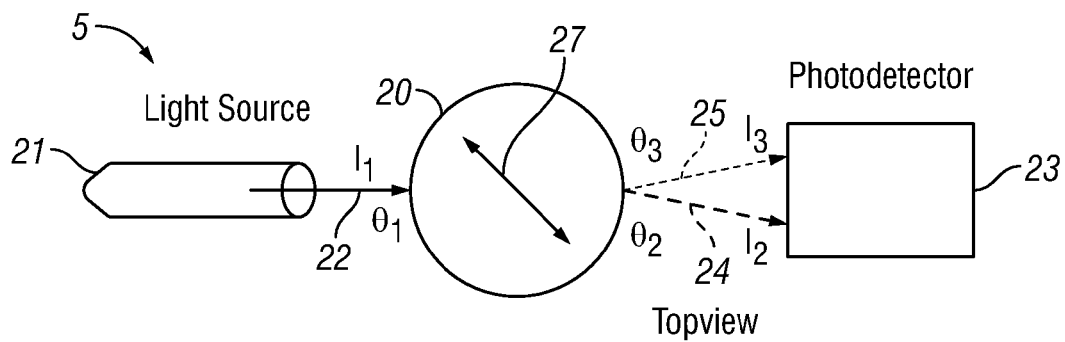

In the embodiment of FIG. 9, the light source 21 and photodetector 23 are in a plane that includes the optical axis 27. Rotation of the light source 21 and the photodetector 23 with respect to the birefringent material 20 causes the optical axis 27 to rotate with respect to the light source 21 and the photodetector 23. Optical characteristics of the ordinary ray 24 and the extraordinary ray 25 depend on the amount of rotation of the optical axis 27. FIG. 9B illustrates a top view of the sensor 5 for demonstrating rotation of the optical axis 27. Referring to FIG. 9B, the incident light ray 22 is parallel to the optical axis 27. Therefore, the birefringent material 20 has no effect on the ordinary ray 24 and the extraordinary ray 25. Referring to FIG. 9C, the incident light ray 22 forms an angle $\theta_1$ with the optical axis 27 greater than zero. Because the angle $\theta_1$ is greater than zero, the exit angle $\theta_2$ of the ordinary ray 24 and the exit angle $\theta_3$ of the extraordinary ray 25 are different from each other. Similarly, the intensity $I_2$ of the ordinary ray 24 and the intensity $I_3$ of the extraordinary ray 25 may be different from each other. In general, the exit angles $\theta_2$ and $\theta_3$ and the intensities $I_2$ and $I_3$ change as the optical axis 27 rotates with respect to the incident light ray 22.

Figure 10:
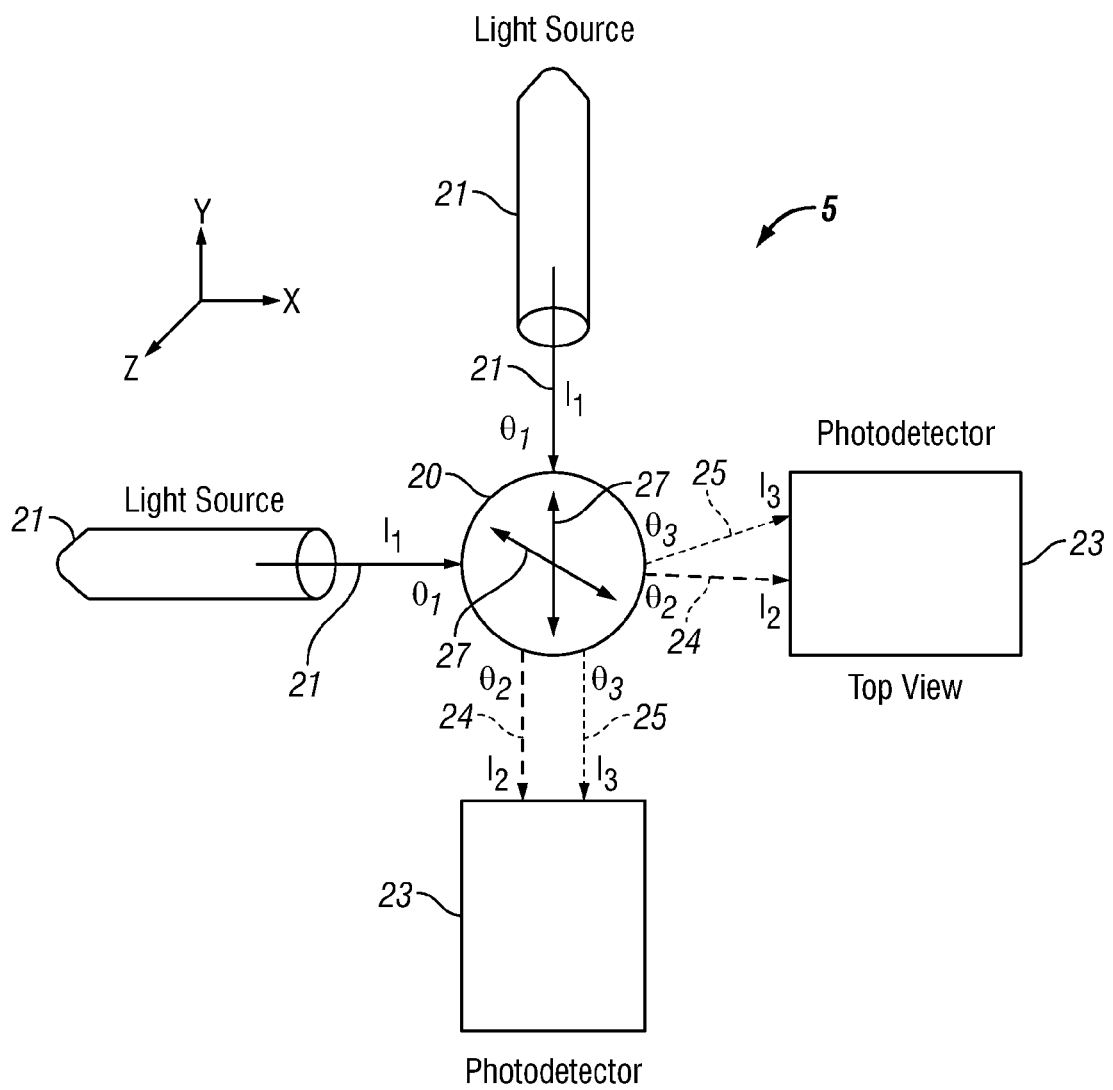
FIG. 10 illustrates exemplary aspects of the sensor for measuring orientation about two axes with a biaxial crystal.

FIG. 10 illustrates an exemplary embodiment of the sensor 5 using a biaxial crystal for the birefringent material 20. As discussed above, the birefringent material 20 that is biaxial has two optical axes 27. Referring to FIG. 10, the sensor 5 includes two light sources 21 and two photodetectors 23. In general, the light sources 21 are rigidly connected to the photodetectors 23. Each of the light sources 21 provides the incident light ray 22 that travels through the birefringent material 20. Each incident light ray 22 is decomposed into the ordinary ray 24 and the extraordinary ray 25. The sensor 5 of the embodiment of FIG. 10 can measure rotation about two axes, the X-axis and the Z-axis. As above, the rotation is measured by measuring the characteristics (such as the exit angles $\theta_2$ and $\theta_3$ and the intensities $I_2$ and $I_3$) for each of the ordinary rays 24 and the extraordinary rays 25.

Typically, the well logging instrument 10 includes adaptations as may be necessary to provide for operation during drilling or after a drilling process has been undertaken.

Figure 11:
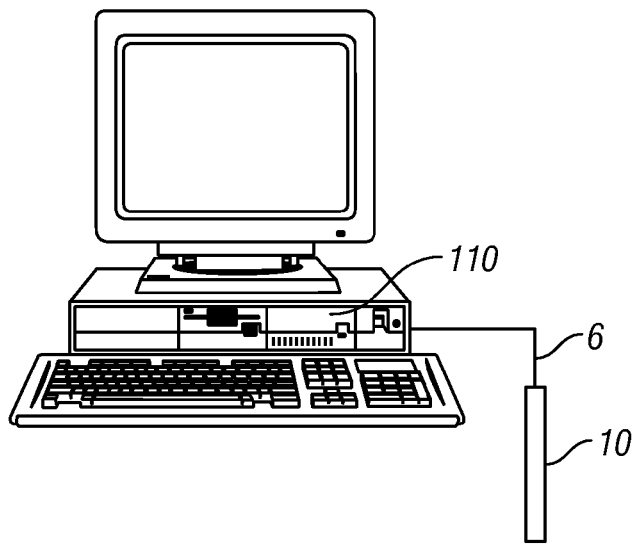
FIG. 11 illustrates an exemplary embodiment of the logging instrument connected to a computer.

Various digital and/or analog systems may be used to operate the sensor 5. An exemplary system including a computer 110 is depicted in FIG. 11. In FIG. 11, the computer 110 is coupled to the well logging instrument 10 that includes the sensor 5. Typically, the computer 110 includes components as necessary to provide for the real time processing of data from the well logging instrument 10. Exemplary components include, without limitation, at least one processor, storage, memory, input devices, output devices and the like. As these components are known to those skilled in the art, these are neither depicted in any detail nor discussed further herein.

Typically, the teachings herein are reduced to an algorithm that is stored on machine-readable media. The algorithm is implemented by the computer 110 and provides operators with desired output. The output is typically generated on a real-time basis.

The sensor 5 may be used to provide real-time measurements of at least one of orientation, acceleration and pressure. As used herein, generation of data in "real-time" is taken to mean generation of data at a rate that is useful or adequate for making decisions during or concurrent with processes such as production, experimentation, verification, and other types of surveys or uses as may be opted for by a user or operator. As a non-limiting example, real-time measurements and calculations may provide users with information necessary to make desired adjustments during the drilling process. In one embodiment, adjustments are enabled on a continuous basis (at the rate of drilling), while in another embodiment, adjustments may require periodic cessation of drilling for assessment of data. Accordingly, it should be recognized that "real-time" is to be taken in context, and does not necessarily indicate the instantaneous determination of data, or make any other suggestions about the temporal frequency of data collection and determination.

A high degree of quality control over the data may be realized during implementation of the teachings herein. For example, quality control may be achieved through known techniques of iterative processing and data comparison. Accordingly, it is contemplated that additional correction factors and other aspects for real-time processing may be used. Advantageously, the user may apply a desired quality control tolerance to the data, and thus draw a balance between rapidity of determination of the data and a degree of quality in the data.

Figure 12:
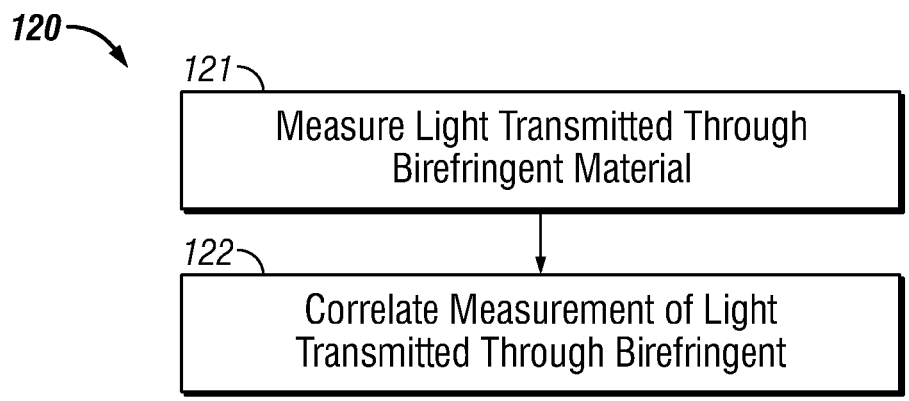
FIG. 12 illustrates an exemplary method for measuring at least one of orientation and force.

FIG. 12 presents an exemplary method 120 for measuring at least one of orientation, acceleration and pressure in the borehole 2. The method 120 calls for using the sensor 5 incorporating the birefringent material 20. A first step 121 calls for measuring light transmitted through the birefringent material 20. Typically, the first step 121 includes measuring the characteristics of the ordinary ray 24 and the extraordinary ray 25. The first step 121 may also include calibrating the birefringent material 20. Calibrating the birefringent material 20 provides the characteristics of the ordinary ray 24 and the extraordinary ray 25 related to a reference. The reference may be one of orientation, force of acceleration, pressure, and force of gravitational acceleration. If the birefringent material 20 is calibrated to an absolute standard, then subsequent measurements may be referenced to the absolute standard. A second step 122 calls for correlating a measurement of light transmitted through the birefringent material 20 to at least one of orientation, acceleration and pressure. Typically, when the sensor 5 measures the force 26, the correlating includes comparing the characteristics of the ordinary ray 24 and the extraordinary ray 25 to calibration information. Typically, when the sensor 5 measures orientation, the correlating includes relating the characteristics of the ordinary ray 24 and the extraordinary ray 25 to an angle the incident light 22 forms with the optical axis 27.

Figure 13:
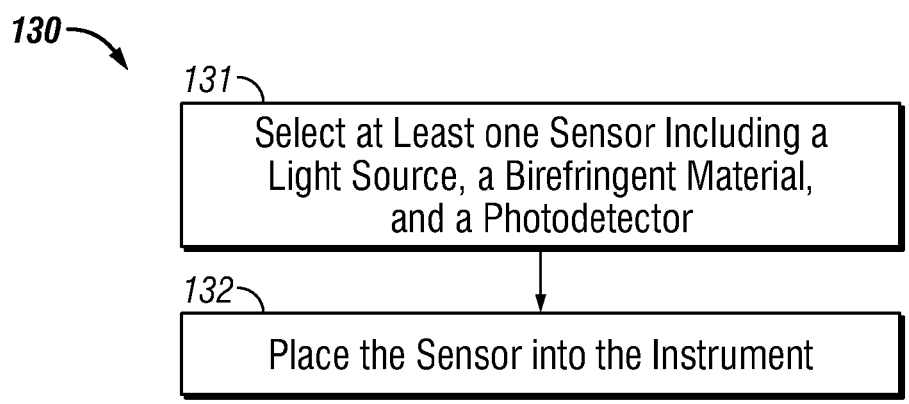
FIG. 13 illustrates an exemplary method for producing the logging instrument.

FIG. 13 presents an exemplary method 130 for producing the logging instrument 10 for measuring at least one of orientation, acceleration and pressure. A first step 131 calls for selecting at least one sensor 5 that includes the light source 21, the birefringent material 20, and the photodetector 23. A second step 132 calls for placing sensor 5 into the logging instrument 10.

In certain embodiments, the sensor 5 may be disposed in more than one logging instrument 10. In these embodiments the responses from the sensors 5 may be combined to produce a composite response. Using multiple instruments 10 to produce the composite response is considered inherent to the teachings herein and a part of the disclosure disclosed.

The sensor 5 may be built for measuring accelerations that are at least one of direction independent and specific to certain axes. The sensor 5 can be built to measure acceleration in one, two, or three axes. For example, a combination of the light source 21, the birefringent material 20, and the photodetector 23 can be used to measure acceleration in one axis. By measuring acceleration along one axis, acceleration along the other two axes can be ignored. By using three of the combinations placed orthogonal to each other, acceleration can be measured in three dimensions. Similarly, the sensor 5 using the uniaxial crystal for the birefringent material 20 can be built to measure orientation or rotation about three axes using three of the combinations.

Figure 14:
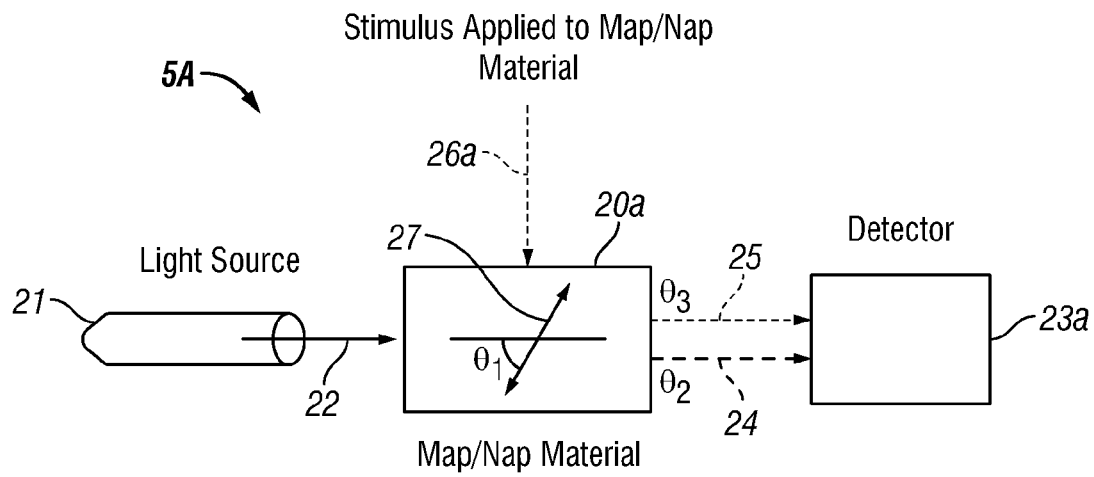
FIG. 14 illustrates an exemplary embodiment of an apparatus according to the present disclosure for measuring a stimulus.

FIG. 14 shows an exemplary embodiment of sensor 5A using a MAP/NAP material 20A tuned to respond to a stimulus 26A, such as a magnetic field. Stimulus 26A may be constant or varying. Electromagnetic source 21 may generate light ray 22 that traverses MAP/NAP material 20A to reach detector 23A. Stimulus 26A may cause a change in the optical axis 27 of the MAP/NAP material 20A such that the light ray 22 is changed when it reaches detector 23A in the form of ordinary ray 24 and extraordinary ray 25. The difference between the rays 24, 25 reaching detector 23A when stimulus is or is not present may be a rotation in polarization. The difference may vary linearly (Faraday Effect and Pockels Effect) or quadratically (Voigt Effect, Cotton-Mouton Effect, and Kerr Effect). Stimulus 26A may or may not result in the flexing or other physical deformation of the MAP/NAP material 20A. In some embodiments, electromagnetic source 21 may be positioned such that light ray 22 may enter MAP/NAP material 20A and be reflected such that rays 24, 25 reach detector 23A.

Referring now to FIGS. 3 and 14, the sensor 5A may be configured to estimate any number of parameters relating to the logging instrument 10, the wellbore 2, and/or the formation 4. The logging instrument 10 is merely illustrative of the wellbore tooling that may utilize the sensor 5A. For example, one or more sensors 5A may also be used in a drilling system conveyed by a rigid carrier or a non rigid carrier. The sensors 5A may also be used in hydrocarbon production systems; e.g., production tubing, intelligent valves, etc. In certain embodiments, the sensor 5A may be configured to estimate a force applied to the logging instrument 10, a drilling assembly (not shown), a force applied to a wellbore wall, or any other applied force (e.g., drill string torsion, drill string vibration, bit bounce, steering forces, thrust forces, etc.). In embodiments, the sensor 5A may be configured to estimate drilling parameters such as drilling direction, position, orientation, etc. (e.g., azimuth, inclination, magnetic north, strength of magnetic fields, casing collar locations, etc.). In embodiments, the sensor 5A may be configured to estimate formation parameters relating to lithology, geophysical parameters, petrophysical parameters, (e.g., resistivity, porosity, etc.). The sensor 5A may also be used to estimate parameters such as pressure and temperature. The sensor 5A may be positioned inside a conveyance device (e.g., a drill string or coiled tubing) or external to the tool 10.

Figure 15:
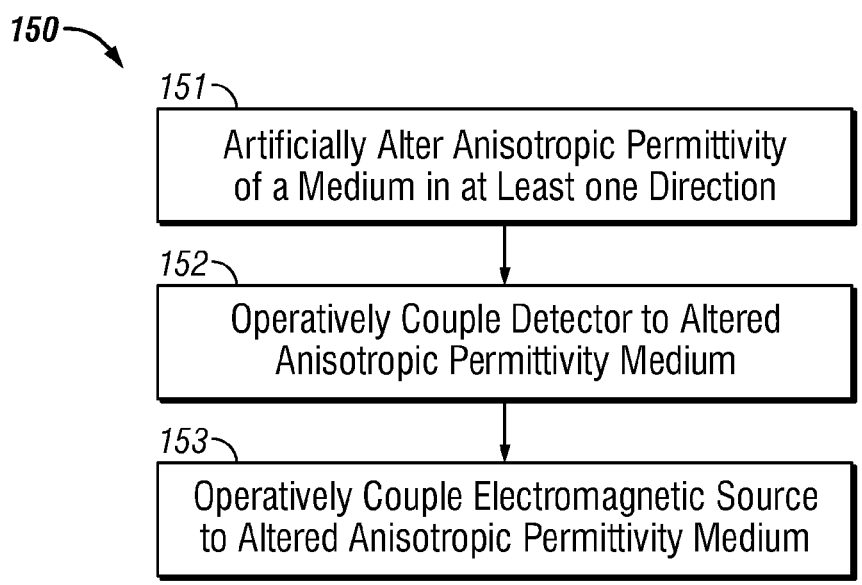
FIG. 15 illustrates an exemplary embodiment of a method according to the present disclosure for manufacturing a sensor.

FIG. 15 shows a method 150, according to one embodiment of the present disclosure, for manufacturing an apparatus 5 for estimating a parameter of interest using a MAP/NAP material. In step 151, a medium may be artificially altered to demonstrate anisotropic permittivity in at least one direction, thus becoming MAP/NAP medium 20. The medium may be a NAP material or a naturally isotropic permittivity material. The alteration of the medium may be specifically tuned such that the medium will respond to one or more selected stimuli. The medium may be tuned to be responsive to one or more of a number of stimuli, including, but not limited to mechanical force, temperature, magnetism, electric potential, electric current, pressure, acceleration, gravity, electromagnetic radiation, nuclear radiation, and vibration. Alteration of permittivity may use techniques known to those of skill in the art. The medium may also be induced to have a uniaxial property or a biaxial property. In step 152, a detector 23, selected for its responsiveness to electromagnetic radiation, may be operatively coupled to the MAP/NAP medium 20. In step 153, an electromagnetic source 21 may be operatively coupled to the MAP/NAP medium 20 such that the electromagnetic source 21 may illuminate detector 23 by transmitting electromagnetic radiation through the MAP/NAP medium 20.

In support of the teachings herein, various analysis components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present disclosure. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, power supply (e.g., at least one of a generator, a remote supply and a battery), refrigeration (i.e., cooling) unit or supply, heating component, motive force (such as a translational force, propulsional force or a rotational force), sensor, transmitter, receiver, transceiver, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the disclosure disclosed.

While the disclosure has been described with reference to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

I claim:

1. An apparatus for use in a borehole, comprising:
 a manufactured anisotropic permittivity material comprising at least one photoresponsive fiber; and
 a detector configured to receive electromagnetic radiation transmitted through the manufactured anisotropic permittivity material and generate a signal in response thereto, wherein the apparatus is configured for use in the borehole.

2. The apparatus of claim 1, further comprising an electromagnetic source configured to transmit electromagnetic radiation into the manufactured anisotropic permittivity material.

3. The apparatus of claim 1, wherein the manufactured anisotropic permittivity material comprises one of: (i) a uniaxial property and (ii) a biaxial property.

4. The apparatus of claim 1, further comprising a proof mass connected to the manufactured anisotropic permittivity material, wherein the signal is indicative of gravitational acceleration.

5. The apparatus of claim 1, wherein the manufactured anisotropic permittivity material is responsive to a stimulus, the stimulus being at least one of: mechanical force, temperature, magnetism, electric potential, electric current, pressure, acceleration, gravity, electromagnetic radiation, nuclear radiation, and vibration.

6. The apparatus of claim 1, wherein the manufactured anisotropic permittivity material comprises a tuned anisotropic permittivity material.

7. A method for estimating a parameter of interest, the method comprising:
 operating a sensor positioned in a borehole, comprising:
  a manufactured anisotropic permittivity material comprising at least one photoresponsive fiber; and
  a detector configured to receive electromagnetic radiation transmitted through the manufactured anisotropic permittivity material and generate a signal in response thereto, wherein the apparatus is configured for use in the borehole.

8. The method of claim 7, further comprising illuminating the manufactured anisotropic permittivity material with electromagnetic radiation.

9. The method of claim 7, further comprising estimating an angle of the electromagnetic radiation transmitted through the manufactured anisotropic permittivity material.

10. The method of claim 7, further comprising calibrating the manufactured anisotropic permittivity material to a reference.

11. The method of claim 7, wherein the manufactured anisotropic permittivity material comprises one of: (i) a uniaxial property and (ii) a biaxial property.

12. The method of claim 7, wherein the manufactured anisotropic permittivity material is responsive to a stimulus, the stimulus being at least one of: mechanical force, temperature, magnetism, electric potential, electric current, pressure, acceleration, gravity, electromagnetic radiation, nuclear radiation, and vibration.

13. The method of claim 7, wherein the parameter of interest is at least one of: mechanical force, temperature, magnetism, electric potential, electric current, pressure, acceleration, gravity, electromagnetic radiation, nuclear radiation, and vibration.

14. The method of claim 7, wherein the manufactured anisotropic permittivity material comprises a tuned manufactured anisotropic permittivity material.

15. A non-transitory computer-readable medium product, comprising:
 a processor; and
 a set of instructions that, when executed, cause the processor to perform a method, the method comprising:
  estimating the parameter of interest using an apparatus comprising:
   a manufactured anisotropic permittivity material comprising at least one photoresponsive fiber; and
   a detector configured to receive electromagnetic radiation transmitted through the manufactured anisotropic permittivity material and generate a signal in response thereto, wherein the apparatus is configured for use in a borehole.

16. The non-transitory computer-readable medium product as in claim 15, wherein the parameter of interest comprises at least one of: mechanical force, temperature, magnetism, electric potential, electric current, pressure, acceleration, gravity, electromagnetic radiation, nuclear radiation, and vibration.

17. A method for manufacturing an apparatus for estimating a parameter of interest, comprising:
 forming the apparatus by operatively coupling a detector and a medium, the medium comprising at least one photoresponsive fiber, wherein the permittivity of the medium has been artificially altered in at least one direction and wherein the apparatus is configured for use in a borehole.

18. The method of claim 17, further comprising:
 operatively coupling an electromagnetic source to the apparatus.

19. The method of claim 17, wherein the artificial alteration of the medium includes tuning the medium to be responsive to a desired stimulus, the desired stimulus including at least one of: mechanical force, temperature, magnetism, electric potential, electric current, pressure, acceleration, gravity, electromagnetic radiation, nuclear radiation, and vibration.

20. The method of claim 17, wherein the artificial alteration of the medium includes inducing one of: (i) a uniaxial property and (ii) a biaxial property.

* * * * *